US010273424B2

(12) United States Patent
Knight et al.

(10) Patent No.: US 10,273,424 B2
(45) Date of Patent: Apr. 30, 2019

(54) ALCOHOL-CONTAINING COMPOSITIONS USEFUL AS SOLID FUELS AND PROCESSES FOR THEIR MANUFACTURE

(71) Applicant: B.C.B. International Limited, Cardiff (GB)

(72) Inventors: David W. Knight, Cardiff (GB); Ian R. Morgan, Cardiff (GB)

(73) Assignee: B.C.B. International Limited, Cardiff (GB)

(*) Notice: Subject to any disclaimer, the term of this patent is extended or adjusted under 35 U.S.C. 154(b) by 817 days.

(21) Appl. No.: 14/383,613

(22) PCT Filed: Mar. 8, 2013

(86) PCT No.: PCT/GB2013/050577
§ 371 (c)(1),
(2) Date: Sep. 8, 2014

(87) PCT Pub. No.: WO2013/132264
PCT Pub. Date: Sep. 12, 2013

(65) Prior Publication Data
US 2015/0111972 A1 Apr. 23, 2015

(30) Foreign Application Priority Data

Mar. 9, 2012 (GB) .................................. 1204205.7
Feb. 20, 2013 (GB) .................................. 1302964.0

(51) Int. Cl.
*A01N 25/04* (2006.01)
*A01N 31/02* (2006.01)
*F23B 30/00* (2006.01)
*C10L 7/04* (2006.01)

(52) U.S. Cl.
CPC ............... *C10L 7/04* (2013.01); *A01N 25/04* (2013.01); *A01N 31/02* (2013.01); *F23B 1/00* (2013.01); *C10L 2200/029* (2013.01); *C10L 2200/0295* (2013.01)

(58) Field of Classification Search
CPC .......... A01N 25/04; A01N 31/02; F23B 30/00
See application file for complete search history.

(56) References Cited

U.S. PATENT DOCUMENTS

| | | | |
|---|---|---|---|
| 718,318 A | 1/1903 | Cronemeyer | |
| 1,266,080 A | 5/1918 | Strobl | |
| 1,277,149 A | 8/1918 | Strobl | |
| 1,389,638 A | 9/1921 | Fisher | |
| 1,484,190 A | 2/1924 | Ray | |
| 1,545,595 A | 7/1925 | Mork et al. | |
| 3,148,958 A | 9/1964 | Monick | |
| 3,183,068 A | 5/1965 | Monick et al. | |
| 3,285,718 A | 11/1966 | Whitfield et al. | |
| 4,261,700 A | 4/1981 | Monick | |
| 4,436,525 A | 3/1984 | Zmoda et al. | |
| 4,461,712 A | 7/1984 | Jonnes | |
| 4,908,044 A | 3/1990 | Brungardt | |
| 5,641,890 A | 6/1997 | Wesley et al. | |
| 5,858,031 A | 1/1999 | Perlman | |
| 5,990,057 A | 11/1999 | Sharp | |
| 6,001,341 A * | 12/1999 | Genova | A61K 8/37 424/401 |
| 6,045,813 A | 4/2000 | Ferguson et al. | |
| 6,432,421 B1 | 8/2002 | Brown et al. | |
| 6,617,294 B2 | 9/2003 | Narula et al. | |
| 6,667,286 B1 | 12/2003 | Dettinger et al. | |
| 6,727,210 B1 | 4/2004 | Perdew, Jr. | |
| 7,354,461 B2 | 4/2008 | Nemeth et al. | |
| 8,101,032 B1 | 1/2012 | Brandenburg et al. | |
| 2005/0271595 A1 | 12/2005 | Brown | |
| 2009/0305914 A1 | 12/2009 | Li et al. | |
| 2011/0217247 A1 | 9/2011 | Lochhead et al. | |

FOREIGN PATENT DOCUMENTS

| | | |
|---|---|---|
| CN | 87107516 A | 8/1988 |
| CN | 1046930 A | 11/1990 |
| CN | 1075158 A | 8/1993 |
| CN | 1084879 A | 4/1994 |
| CN | 1100457 A | 3/1995 |
| CN | 101643679 A | 2/2010 |
| CN | 101717680 A | 6/2010 |
| CN | 101879171 A | 11/2010 |
| CN | 102178658 * | 9/2011 |

(Continued)

OTHER PUBLICATIONS

CN102178658—machine-translation, 2011, machine translation of CN102178658.*
Database WPI, Week 200420, Thomson Scientific, London, GB; AN 2004-207211 XP002699682, & JP 2004 026725 A (Sunstar Chem Ind Co Ltd) Jan. 29, 2004 (Jan. 29, 2004).
Database WPI, Week 199130, Thomson Scientific, London, GB; AN 1991-215726 XP002699656, & CN 1 046 930 A (Zhang Bin) Nov. 14, 1990 (Nov. 14, 1990).
Butanone; Wikipedia; Feb. 6, 2013.
Erythritol; Wikipedia; Oct. 23, 2012.

(Continued)

*Primary Examiner* — Sun Jae Yoo

(74) *Attorney, Agent, or Firm* — McCarter & English, LLP; Steven G. Davis; Wei Song

(57) ABSTRACT

There is provided a composition comprising: (a) from about 60 to about 98% by weight of one or more alcohols; (b) from about 0.5 to about 20% by weight of one or more alkyl cellulose derivatives, wherein each alkyl is optionally substituted with one or more OH, O-alkyl, O-hydroxyalkyl and/or O-alkoxyalkyl; (c) from about 1 to about 25% by weight of one or more carboxylic acid salts; and (d) from 0 to about 30% by weight of water. There is also provided uses, processes for manufacture, methods and products relating to the same.

11 Claims, 2 Drawing Sheets

(56) References Cited

FOREIGN PATENT DOCUMENTS

| | | |
|---|---|---|
| DE | 10137865 A1 | 5/2002 |
| ES | 0472353 A1 | 3/1979 |
| ES | 2095797 A1 | 2/1997 |
| FR | 2690084 A1 | 10/1993 |
| GB | 191202137 A | 8/1912 |
| GB | 1251002 A | 10/1971 |
| GB | 1438944 A | 6/1976 |
| GB | 2401374 A | 11/2004 |
| JP | 10-30098 | 2/1998 |
| JP | 2004/026725 A | 1/2004 |
| JP | 2004/210841 A | 7/2004 |
| JP | 2005/190975 A | 7/2005 |
| KR | 20100042320 A | 4/2010 |
| NL | 1022643 C1 | 8/2004 |
| WO | 2000/78857 A1 | 12/2000 |
| WO | 2003/040272 A1 | 5/2003 |
| WO | 2003/068896 A1 | 8/2003 |
| WO | 2003/074935 A2 | 9/2003 |
| WO | 2005/037961 A2 | 4/2005 |
| WO | 2006/028667 A1 | 3/2006 |
| WO | 2006/052243 A1 | 5/2006 |
| WO | 2006/085907 A2 | 8/2006 |
| WO | 2006/107983 A2 | 10/2006 |
| WO | 2008/095319 A1 | 8/2008 |
| WO | 2008/106502 A2 | 9/2008 |
| WO | 2010/047022 A1 | 4/2010 |
| WO | 2010/132209 A1 | 11/2010 |
| WO | 2011/094340 A1 | 8/2011 |

OTHER PUBLICATIONS

Ethanol Terms; Table; www.alcohols.co.uk/ethanol_terms.php, Feb. 7, 2013.
German Search Report for GB Application No. 1204205.7 dated Jun. 21, 2012.
Hypromeliose; Wikipedia; Jan. 8, 2012.
International Preliminary Report on Patentability for PCT Application No. PCT/GB2013/050577 dated Sep. 9, 2014.
International Search Report for PCT Application No. PCT/GB2013/050577 dated Jul. 8, 2013.
Methyl cellulose; Wikipedia; Jan. 29, 2012.
Proposed Change to Formulation for Completely Denatured Alcohol; HM Revenue & Customs; Publication date: Nov. 9, 2012.

* cited by examiner

ALCOHOL-CONTAINING COMPOSITIONS USEFUL AS SOLID FUELS AND PROCESSES FOR THEIR MANUFACTURE

The present invention relates to novel alcohol-containing compositions, methods of producing such compositions, and uses, methods and products relating to the same.

In particular, the present invention relates to compositions comprising an organic alcohol, a non-ionic cellulose derivative and a carboxylic acid salt, which compositions may be useful as solid fuels.

The listing or discussion of a prior-published document in this specification should not necessarily be taken as an acknowledgment that the document is part of the state of the art or is common general knowledge.

Fluid fuels (such as liquids and gases) are routinely used for heating and cooking purposes in circumstances where a transportable and easy to use fuel source is required. Such fuels can also be used in the domestic environment, for example in cases where a mains supply of gas and/or electricity is not available, or outdoors (for example, as part of camping equipment).

The use of fluid fuels, in contrast to the use of various solid fuels, has advantages including increased ease of combustion. Further, the combustion of fluid fuels (particularly liquids) typically provides a higher energy yield than combustion of naturally-occurring solid fuels (such as wood and coal).

Nevertheless, although liquid fuels are typically easier to handle than gases, the high degree of flowability inherent in such substances creates significant risks associated with the potential for leakage during transport and use. Moreover, as flammable liquids are typically highly volatile, the use of most fluid fuels poses significant hazards resulting from the potential for the leakage of flammable gases.

As an alternative to the use of fluid fuels, synthetic solid fuels have been developed. An example of an artificial solid fuel is the hexamine fuel tablet, which consists of a mixture of hexamine (hexamethylenetetramine) and 1,3,5-trioxane, and which is sold commercially as Esbit®. However, the use of hexamine fuel tablets has numerous disadvantages. For example, combustion of such fuel tablets is known to result in the production of highly toxic gases (such as formaldehyde, ammonia, nitrogen oxide and hydrogen cyanide), ingestion of which may lead to nausea, vomiting, gastrointestinal disturbances, kidney damage and, if ingested in sufficient quantities, death (see the Material Data Safety Sheet (MSDS) for Esbit®).

The use of liquid fuels having increased viscosity has also been investigated. Such fuels have been produced, for example, through the use of thickening agents to create viscous solutions of ethanol and/or methanol. However, although such fuels are often referred to as "gels", these compositions are not gels in accordance with the true meaning of the term. This is because, although they may be highly viscous, they exhibit a degree of flow. As a result, such compositions do not eliminate disadvantages associated with fluid fuels. For example, these flammable compositions may leak from packaging materials and contaminate surrounding areas, thereby creating a risk to safety during transport and/or use.

In view of the above, it can be seen that there remains a need for alternatives to existing fuel sources, particularly alternatives that avoid the above-mentioned disadvantages.

We have now found, surprisingly, that such a fuel source may be obtained by the use of compositions comprising one or more organic alcohols, one or more non-ionic cellulose derivatives, one or more carboxylic acid salts and, optionally, water.

Thus, according to a first aspect of the invention there is provided a composition comprising:
(a) from about 60 to about 98% by weight of one or more alcohols;
(b) from about 0.5 to about 20% by weight of one or more alkyl cellulose derivatives, wherein each alkyl is optionally substituted with one or more OH, O-alkyl, O-hydroxyalkyl and/or O-alkoxyalkyl;
(c) from about 1 to about 25% by weight of one or more carboxylic acid salts; and
(d) from 0 to about 30% by weight of water, which compositions are herein referred to as "compositions of the invention".

In respect of the first aspect of the invention, the percentage of components (a) to (d) is a percentage by weight of the combined weight of components (a) to (d) in the composition. In other words, the presence of other components (i.e. other than components (a) to (d)) in the composition is not relevant to the calculation of the percentage of components (a) to (d) present in the composition. Further, each percentage represents the total amount of the corresponding component present in the composition. For example, the respective percentages of components (a) to (d) include all substances falling under the definition of each component that is present in the composition.

In particular, the skilled person will understand that, by virtue of their amounts being defined as a percentage, the combined total of the percentages indicated in respect of components (a) to (d) will equal 100% (i.e. the combined total cannot exceed 100%).

Further, the skilled person will understand the term "about" to mean within a reasonable degree of accuracy of the amount indicated. For example, where a percentage is indicated as a whole number, this may include amounts that correspond to said amount when rounded up or down (as appropriate) to the nearest whole number. Moreover, where a percentage is indicated to one decimal place, this may include amounts that correspond to said amount when rounded up or down (as appropriate) to a value indicated to one decimal place. As such, the term "about" may be deleted from definitions provided herein without changing the meaning of the respective definition.

In respect of component (d), the skilled person will understand that 0% indicates that no appreciable amount of said component is present in the composition. In particular, the skilled person will understand that 0% indicates that none of the relevant component was added during preparation of the composition. As a result, the composition may also be described as "optionally" comprising component (d).

In an alternative embodiment of the first aspect of the invention, certain compositions may be described as "essentially water free". In this context, the term "essentially water free" can be taken as referring to compositions comprising less than 5% by weight of water (such as less than 2%, particularly less than 1%, and more particularly less than 0.1% by weight).

Unless otherwise specified, $C_{1-q}$ alkyl groups (where q is the upper limit of the range) defined herein may be straight-chain (i.e. linear) or, when there is a sufficient number (i.e. a minimum of three, as appropriate) of carbon atoms, be branched-chain (i.e. branched). The same applies to the alkyl portion of alkoxy and hydroxyalkyl groups.

Unless otherwise specified, $C_{1-q}$ alkenyl groups (where q is the upper limit of the range) defined herein may be straight-chain (i.e. linear) or, when there is a sufficient number (i.e. a minimum of four, as appropriate) of carbon atoms, be branched-chain (i.e. branched).

Unless otherwise specified, $C_{1-q}$ alkynyl groups (where q is the upper limit of the range) defined herein may be straight-chain (i.e. linear) or, when there is a sufficient number (i.e. a minimum of five, as appropriate) of carbon atoms, be branched-chain (i.e. branched).

In particular embodiments of the first aspect of the invention, components (a) to (d) are as indicated below.

Component (a)

The term "alcohol" will be well understood by those skilled in the art as referring to a compound containing an OH group bound to an organic moiety (i.e. containing a C—OH moiety).

When used herein, the term "organic" includes references to uncharged chemical compounds (other than carbon, oxides of carbon, or acids of (bi)carbonate, cyanide, cyanate, thiocyanate or fulminate), whose molecules contain carbon.

The term "uncharged", when used herein in relation to component (a), refers to alcohols that do not bear a permanent positive or negative (electrostatic) charge on any atom within the molecule. In this respect, uncharged organic compounds are those that comprise a single, covalently-bonded molecule and that are not separated into cationic and anionic components.

In a particular embodiment of the first aspect of the invention, component (a) consists of one or more $C_1$-$C_8$ (e.g. $C_{1-6}$, $C_{1-5}$, $C_{1-4}$, $C_{1-3}$ or $C_{1-2}$, such as $C_1$ or $C_2$) linear or, where possible, branched (e.g. linear) alkyl moieties substituted with at least one (such as two or, particularly, one) hydroxyl group(s).

The skilled person will appreciate that alcohols (or mixtures of alcohols) that are particularly useful for the preparation of fuels are typically liquid at room temperature at atmospheric pressure (i.e. substances that have a melting point that is significantly lower than room temperature and a boiling point that is higher than room temperature).

Thus, in a particular embodiment, component (a) is one or more liquid alcohols. As used herein, the term liquid alcohols will be understood to refer to an alcohol, as defined herein, that is a liquid (i.e. a substance of definite volume but no fixed shape) at room temperature (i.e. around 20° C.) and at atmospheric pressure (i.e. around 100 kPa).

In a further embodiment, component (a) consists of one or more (e.g. one or two) alcohols selected from the group consisting of: n-butanol and, in particular, ethanol, methanol and 2-propanol; and/or the alcohol component of industrial methylated spirits.

For example, component (a) may consist of the alcohol component of industrial methylated spirits (IMS). In this regard, the skilled person will understand that "industrial methylated spirits" refers to the commercially-available substances commonly marketed under that name, and which typically comprise denatured ethanol (i.e. a mixture of ethanol and methanol) and optionally one or more taste modifier (e.g. a bittering agent), colorant, agent that causes the solution become undrinkable and/or agent intended to hamper attempts to reverse the denaturing process. In particular, IMS may contain pyridine and/or one or more ketone (such as acetone).

Embodiments of the first aspect of the invention that may be mentioned include those wherein component (a) consists of:
 ethanol;
 a mixture of ethanol and 2-propanol (e.g. wherein the mixture consists of about 0.5 to 10% (such as about 5%) by weight of 2-propanol and the remainder of the mixture is ethanol); or
 a mixture of ethanol and methanol (such as denatured ethanol, and/or wherein the mixture consists of about 0.5 to 20% (such as about 10%) by weight of methanol and the remainder of the mixture is ethanol).

In particular, component (a) may be incorporated in the composition in the form of fermentation grade ethanol, wherein the ethanol is present in an amount that is around 95 to 96% by weight or volume of the total of component (a) (i.e. the ethanol used is not pure (i.e. absolute) ethanol).

For example, the composition of component (a) may result from the use of the grade of ethanol known commercially as TSDA 7 (or TSDA(IPA)), which typically comprises about 5.0% by volume of isopropyl alcohol (IPA; i.e. 2-propanol).

For the avoidance of doubt, the skilled person will understand that component (a) may be added to the composition in a form that also contains other non-alcohol components, which components may relate to any of components (b) to (d) and/or and be regarded as additives as herein described. In particular, component (a) may be added in the form of an alcohol containing one or more denaturing agents, such as those described herein below.

For example, component (a) may be added to the composition in the form of the product commonly known in the United Kingdom as completely denatured alcohol (CDA), which in its newly-adopted formulation typically comprises approximately 94.2% by volume ethanol, 2.8% by volume 2-propanol and 2.8% by volume butanone (i.e. 2-butanone, also known as methyl ethyl ketone (MEK)), optionally together with small amounts of denatonium benzoate (Bitrex®; around 1 g per 106 L CDA) and, in some cases, methyl violet (around 1.5 g per 1000 L CDA).

Particular ethanol containing products that may be mentioned include TSDA 1 to 11, industrial denatured alcohol (IDA, such as UK standard IDA) and UK duty free spirits (as described in UK HMRC Reference:Notice 47 (published January 2012)).

In further embodiments of the first aspect of the invention (including in respect of the embodiments referred to above), component (a) may be present in an amount that is about 65 to 95% by weight (i.e. the percentage by weight of the combined weight of components (a) to (d) in the composition), such as:
70 to 92% or, particularly, 75 to 90% (e.g. 79 to 89% or 79 to 90%) by weight; or
70 to 95% or, particularly, 75 to 95% (e.g. 79 to 95%) by weight.

In particular, component (a) may be present in an amount that is about 85 to 98%, such as about 89 to 95%, e.g. about 90% (particularly 89.8%) or about 94% (particularly 94.1%) by weight.

For example, in respect of component (a), the composition may consist of:
about 85% (e.g. 85.2%) by weight of ethanol and about 5% (e.g. 4.7%) by weight of 2-propanol; or
about 91% (e.g. 91.2%) by weight of ethanol and about 3% (e.g. 2.9%) by weight of 2-propanol,
wherein the percentage weights are calculated based on the total weight of components (a) to (d) in the composition.

Component (b)

The term "alkyl cellulose derivative", when used herein in relation to component (b), refers to chemical compounds derived from cellulose wherein a proton on at least some of the cellulose hydroxy groups has been replaced with an alkyl group.

When used herein in respect of the component (b), the term "alkyl" refers to linear or branched (saturated) alkyl chains (e.g. $C_{1-6}$ alkyl, such as $C_{1-3}$ alkyl chains), optionally substituted as defined above (e.g. with one or more —OH group, such as one —OH group). In a particular embodiment, component (b) may be referred to as consisting of one or more O-alkyl cellulose derivatives and/or O-hydroxyalkyl cellulose derivates, particularly wherein the term "alkyl" refers to $C_{1-6}$ (e.g. $C_{1-5}$, $C_{1-4}$ or $C_{1-3}$) alkyl groups and the term "hydroxyalkyl" refers to $C_{1-6}$ (e.g. $C_{1-5}$, $C_{1-4}$ or $C_{1-3}$) alkyl groups substituted with one or more (e.g. one) OH group.

The (mean) average number of substituted hydroxyl groups per monomer in the cellulose polymer (i.e. per glucose molecule) may be referred to as the degree of substitution (DS). In respect of component (b), the alkyl cellulose derivative will typically have a DS of from 0.2 to 3 (such as from 1 to 2.8, e.g. from 1.3 to 2.6).

For example, component (b) may consist of one or more cellulose derivatives represented by formula I,

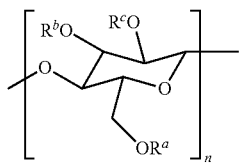

I wherein: each of $R^a$ to $R^c$ is independently H or a $C_{1-6}$ (e.g. $C_{1-5}$, $C_{1-4}$ or $C_{1-3}$) alkyl group optionally substituted with one or more (e.g. one) OH group, provided that at least one of $R^a$ to $R^c$ is other than H in at least 20% (e.g. at least 30, 40, 50 or 60%) of the monomers present; and n is a suitable integer representing the number of glucose monomers present in the cellulose polymer.

In a more particular embodiment, component (b) consists of one or more (e.g. one or two) cellulose derivatives selected from the group consisting of hydroxyethyl cellulose, hydroxyethyl methyl cellulose, methyl cellulose, hydroxypropyl cellulose and hydroxypropylmethyl cellulose.

In particular, component (b) may consist of one or more (e.g. one or two, such as one) cellulose derivates selected from the group consisting of methyl cellulose, hydroxypropyl cellulose and hydroxypropylmethyl cellulose.

More particularly, component (b) may consist of hydroxypropylmethyl cellulose (HPMC).

In further embodiments of the first aspect of the invention (including in respect of the embodiments referred to above), component (b) may be present in an amount that is about 0.7 to 10% by weight (i.e. the percentage by weight of the combined weight of components (a) to (d) in the composition), such as 0.8 to 5% or, particularly, 1 to 3% (e.g. 1.1 to 2.5%) by weight.

In particular, component (b) may be present in an amount that is about 0.8 to 1.6%, such as about 1.1 to 1.3% (e.g. about 1.2%) by weight.

Component (c)

The term "carboxylic acid salt", when used herein in relation to component (c), refers to molecules (compounds) that contain at least one negatively-charged carboxylate group (i.e. a carboxylic acid group in respect of which the acidic proton has been removed) with a positively-charged counter ion (particularly a positively-charged metal ion). Such compounds may also be referred to as carboxylates and/or carboxylate salts.

In a particular embodiment of the first aspect of the invention, component (c) consists of one or more (such as one or two) carboxylic acid salts having a counter ion selected from the group consisting of $Ca^{2+}$, $Li^+$, $K^+$ and $Na^+$. In particular, component (c) may consist of one or more (such as one or two) carboxylic acid salts wherein the counter ion is $Na^+$.

In a further embodiment, component (c) consists of one or more (such as one or two, e.g. two) carboxylic acid salts formed from $C_{10-20}$ (e.g. $C_{12-20}$, $C_{10-18}$, $C_{14-20}$ or $C_{14-18}$, such as $C_{16-18}$ or $C_{16}$ and/or $C_{18}$) alkyl, $C_{10-20}$ (e.g. $C_{12-20}$, $C_{10-18}$, $C_{14-20}$ or $C_{14-18}$, such as $C_{16-18}$ or $C_{16}$ and/or $C_{18}$) alkenyl or $C_{10-20}$ (e.g. $C_{12-20}$, $C_{10-18}$, $C_{14-20}$ or $C_{14-18}$, such as $C_{16-18}$ or $C_{16}$ and/or $C_{18}$) alkynyl carboxylic acids. In particular, component (c) may consist of one or more (such as one or two) carboxylic acid salt obtainable from (e.g. formed from) a $C_{10-20}$ (e.g. $C_{12-20}$, $C_{10-18}$, $C_{14-20}$ or $C_{14-18}$, such as $C_{16-18}$ or $C_{16}$ and/or $C_{18}$) alkyl (in particular, a linear alkyl) having one carboxylic acid moiety. More particularly, component (c) may consist of one or more (such as one or two, e.g. two) carboxylic acid salts obtainable from (e.g. formed from) a $C_{10-18}$ linear alkyl having one carboxylic acid moiety.

In a further embodiment, component (c) consists of at least two (e.g. three or, particularly, two) different carboxylic acid salts (such as those described in the above-mentioned embodiments, e.g. the embodiment mentioned directly above).

As used herein in respect of carboxylic acid salts, the term "different" includes references to the carboxylic acid salts referred to having different chemical structures. In particular, the term may refer to carboxylic acid salts formed from carboxylic acids having different chemical structures (e.g. different empirical chemical formulae). Mixtures of (at least two) different carboxylic acid salts may be obtained by forming salts of carboxylic acids obtained from natural sources, such as plant and animal oils/fats (e.g. hydrogenated and saponified animal fats, such as Pristerine™, and/or hydrogenated and saponified palm oil). In particular, component (c) may consist of a mixture of different carboxylic acid acids, such as a mixture consisting of predominantly (e.g. ≥90% by weight) $C_{16}$ and $C_{18}$ carboxylic acid salts, such as the relevant sodium salts (and wherein the remainder may consist of corresponding $C_{14}$, $C_{15}$ and/or $C_{17}$ carboxylic acid salts).

For example, carboxylic acid salts falling under the definition of component (c) may be represented by formula II, $$[R-C(O)O^-]_n M^{n+}$$ II wherein: R represents $C_{10-20}$ (e.g. $C_{12-20}$, $C_{10-18}$, $C_{14-20}$ or $C_{14-18}$, such as $C_{16-18}$ or $C_{16}$ and/or $C_{18}$) alkyl, $C_{10-20}$ (e.g. $C_{12-20}$, $C_{10-18}$, $C_{14-20}$ or $C_{14-18}$, such as $C_{16-18}$ or $C_{16}$ and/or $C_{18}$) alkenyl or $C_{10-20}$ (e.g. $C_{12-20}$, $C_{10-18}$, $C_{14-20}$ or $C_{14-18}$, such as $C_{16-18}$ or $C_{16}$ and/or $C_{18}$) alkynyl (in particular, $C_{10-20}$ (e.g. $C_{12-20}$, $C_{14-20}$ or $C_{14-18}$, such as $C_{16-18}$ or $C_{16}$ and/or $C_{18}$) alkyl); M represents a metal selected from the group consisting of Ca, Li, K and Na (in particular, Na);

where M represents Li, K and Na, n represents 1; and where M represents Ca, n represents 2.

In a particular embodiment, component (c) consists of two or more different carboxylic acid salts defined by formula II above (e.g. two salts defined by a different formula II).

In a more particular embodiment, component (c) consists of one or two carboxylic acid salts selected from the group consisting of sodium palmitate and sodium stearate.

In particular, component (c) may consist of:
a mixture of sodium palmitate and sodium stearate (such as a roughly equal mixture); or sodium stearate.

In further embodiments of the first aspect of the invention (including in respect of the embodiments referred to above), component (c) may be present in an amount that is about 1 to 15% by weight (i.e. the percentage by weight of the combined weight of components (a) to (d) in the composition), such as 2 to 10% or, particularly, 3 to 6% (e.g. 3.7 to 5.4%) by weight.

In particular, component (c) may be present in an amount that is about 3 to 5% (e.g. about 4 to 5%, such as about 4.4% or about 4.6%) by weight.

Component (d)

In further embodiments of the first aspect of the invention, the amount of component (d) is 0 to about 25% by weight (i.e. the percentage by weight of the combined weight of components (a) to (d) in the composition), such as 0 to 20.0% or, particularly, 0 to 15.0% (e.g. 0 to 14.8%) by weight.

In yet further embodiments, component (d) may be present in an amount that is about 1 to 25% by weight, such as 2 to 20% or, particularly, 4 to 15% or 5 to 15% (e.g. 5.6 to 14.8% or 4.7 to 14.8%) by weight.

In particular, component (d) may be present in an amount that is about 3 to 6% (such as about 4 to 5%, e.g. about 4.5%) by weight.

Alternatively, component (d) may be present in an amount that is less than about 10%, 8% or 6% by weight; for example, less than about 5% (such as less than about 2%, e.g. less than about 1%) by weight.

Thus, in certain cases, there may be provided compositions that may be described as being substantially anhydrous (i.e. containing less than 1% (e.g. less than 0.5%, such as less than 0.1%) by weight of water (i.e. component (d))).

In particular embodiments of the first aspect of the invention, there is provided a composition comprising:
(a) from about 60 to about 98% (such as about 65 to 95%, 70 to 92% or, particularly, 75 to 90%) by weight of
    (i) one or more alcohols selected from the group consisting of ethanol, methanol and 2-propanol, or
    (ii) the alcohol component of industrial methylated spirits;
(b) from about 0.7 to 10% (such as 0.8 to 5% or, particularly, 1 to 3%) by weight of one or more (e.g. one or two) cellulose derivatives selected from the group consisting of hydroxyethyl cellulose, hydroxyethyl methyl cellulose, methyl cellulose, hydroxypropyl cellulose and hydroxypropylmethyl cellulose;
(c) from about 1.5 to 15% (such as 2 to 10% or, particularly, 3 to 6%) by weight of one or more carboxylic acid salts selected from the group consisting of sodium palmitate and sodium stearate (such as a roughly equal mixture of sodium palmitate and sodium stearate); and
(d) from 0 to about 25% (such as 0 to 20% or, particularly, 0 to 15%) by weight, or alternatively about 1 to 25% (such as 2 to 20% or, particularly, 5 to 15%) by weight, of water.

In a certain embodiment of the first aspect of the invention, the composition further comprises one or more additives selected from the group consisting of colorants (such as methyl violet (also known as meths colorant) and/or malachite green), stabilizing agents, taste modifiers (such as bitter tasting substances, e.g. denatonium benzoate (Bitrex®)) and antibacterial agents (such as Triclosan and/or antibacterial agents derived from natural sources, such as tea tree oil).

In particular, the composition may comprise one or more antimicrobial and/or antifungal agents. Particular examples of antimicrobials/antifungals that may be mentioned include:
    agents derived from natural sources, such as tea tree oil, lavender oil and/or citronellol (and other terpene-related compounds);
    chlorohexidine and/or triclosan;
    quinolones;
    tetracycline antibiotics; and
    sulphonamides.

In certain embodiments, the composition may further comprise activated charcoal (e.g. general purpose grade activated charcoal). For example, activated charcoal may be added to the composition in an amount that is up to about 3% (e.g. up to about 2.4%), such as about 1 to 3% (e.g. about 1.2 to 2.4%, such as 1.2%) by weight of the total weight of components (a) to (d) in the composition.

In certain embodiments, the composition further may further comprise one or more metal (such as a transition metal), for example in the form of a powder. In such cases, the addition of a small amount of a suitable metal (e.g. as a fine powder) may result in a composition that burns with a coloured flame, wherein the colour of the flame is dependent on the type of metal used. In particular, such metals may be present in an amount that is up to 5% by weight of the combined weight of components (a) to (d) in the composition.

For the avoidance of doubt, the skilled person will understand that the source of component (a) as used in the composition may itself comprise certain additives, which additives may then form part of the compositions of the invention. In this regard, a particular source of component (a) that may be mentioned is denatured alcohol and, therefore, particular additives that may be mentioned include corresponding denaturing agents (i.e. agents added with the purpose of making the alcohol unpalatable and/or non-ingestible).

Particular denaturing agents that may be mentioned include butanone (i.e. 2-butanone; otherwise known as methyl ethyl ketone (MEK)).

In particular, denaturing agents (e.g. butanone) may be present in compositions of the invention in amounts that are from about 0.1% to 5%, such as about 1% to 4% (e.g. about 2 to 3%, such as about 3% (e.g. 2.9%)) by weight of the total weight of components (a) to (d) in the composition.

Moreover, denaturing agents may be used in combination with colorants. Particular colorants that may be mentioned include methyl violet.

In particular embodiments, the composition may comprise one or more (e.g. one) taste modifier, such as denatonium benzoate (Bitrex®). For example, in certain embodiments a small amount (e.g. less than 0.1%, such as about 0.08%) of component (a) may be replaced with a solution (e.g. a 0.256% by weight solution) of denatonium benzoate.

For the avoidance of doubt, as with all embodiments mentioned herein, each of the above-mentioned embodiments may be taken alone or in combination. For example, compositions may comprise more than one of the above-mentioned additives (e.g. a taste modifier and activated charcoal, or a denaturing agent and activated charcoal, and so on). In particular, compositions of the invention may comprise both butanone and denatonium benzoate.

In particular embodiments, the total amount of additives (i.e. components other than components (a) to (d)) present in compositions of the invention may be up to about 10%, such as up to about 5% (e.g. up to about 3%) by weight of the total weight of components (a) to (d) in the composition.

In an alternative embodiment of the first aspect of the invention, there is provided a composition consisting of components (a) to (d) as defined in respect of any embodiment referred to above (and, optionally, a colorant, stabilizing agent, taste modifier, antibacterial agent, denaturing agent, antifungal agent, powdered metal(s) and/or activated charcoal as defined above, such as a colorant, stabilizing agent, taste modifier and/or antibacterial agent).

Compositions of the invention may be obtained by forming a homogenous mixture of components (a) to (d) as defined in respect of the first aspect of the invention.

Thus, according to a second aspect of the invention there is provided a composition obtainable via a process involving forming a homogenous mixture of:
(a) from about 60 to about 98% by weight of one or more organic alcohols;
(b) from about 0.5 to about 20% by weight of one or more alkyl cellulose derivatives, wherein each alkyl is optionally substituted with one or more OH, O-alkyl, O-hydroxyalkyl and/or O-alkoxyalkyl;
(c) from about 1 to about 25% by weight of one or more carboxylic acid salts; and
(d) from 0 to about 30% by weight of water.

Moreover, according to a third aspect of the invention, there is provided a process for preparing a composition as defined in the first aspect of the invention, wherein the process comprises forming a homogenous mixture of:
(a) from about 60 to about 98% by weight of one or more organic alcohols;
(b) from about 0.5 to about 20% by weight of one or more alkyl cellulose derivatives, wherein each alkyl is optionally substituted with one or more OH, O-alkyl, O-hydroxyalkyl and/or O-alkoxyalkyl;
(c) from about 1 to about 25% by weight of one or more carboxylic acid salts; and
(d) from 0 to about 30% by weight of water.

In respect of the second and third aspects of the invention, the percentage of components (a) to (d) is a percentage by weight of the combined weight of components (a) to (d) introduced in order to form the mixture (i.e. in the complete process). Further, each percentage represents the total amount of the corresponding component utilised as part of the process.

The components (a) to (d) may be mixed in any order. For example, at least some or all of components (a), (b) and (d) may be mixed together first and then component (c) (and, if relevant, the remainder of components (a), (b) and (d)) added to the mixture so formed. As another example, at least some or all of components (a) to (d) may be mixed together simultaneously.

The term "homogeneous", when used herein in relation to the present invention, refers to a composition having (or appearing to have) only one phase. In other words, visual inspection of the material (composition) will not allow for identification of separate materials within the composition. Such compositions may also be referred to as being monophasic (i.e. having (or appearing to have) only one phase).

In particular embodiments of the second and third aspects of the invention, the nature and amount of each of components (a) to (d) is as defined in respect of any embodiment of the first aspect of the invention.

The process for obtaining compositions of the invention may comprise the steps of heating a mixture comprising at least part of each of components (a) to (d) until the mixture becomes homogenous, and then cooling the mixture so obtained.

Thus, in a particular embodiment of the second and third aspects of the invention, the process for forming the composition comprises the steps of:
(i) heating a mixture comprising at least some of (e.g. all of) each of components (a) to (c) and, where present, component (d), until the mixture becomes homogenous; and
(ii) cooling the mixture so obtained.

In particular embodiments of the second and third aspects of the invention that may be mentioned:
step (i) is performed whilst the mixture is being stirred; and/or
step (ii) is performed in a mould defining a desired shape for the cooled mixture.

In a more particular embodiments of the second and third aspects of the invention, step (i) consists of the steps of:
(ia) heating a mixture of at least some of (e.g. all of) each of components (a) and (b) and, where present, component (d), until component (b) is dissolved in component (a); and then
(ib) adding at least some of (e.g. all of) component (c) and heating until the mixture becomes homogenous.

As used herein, the term "dissolved" refers to a state where none of the substance being dissolved is visible as a solid in the solution. As a result, the term includes references to a "homogenous" mixture being formed.

In respect of the above-mentioned embodiment, it is specifically contemplated that:
steps (ia) and/or (ib) may be performed whilst the mixture is being stirred;
where component (d) is present in the composition, all of component (d) is present in step (i) (or, where relevant, step (ia)).

In a further embodiment of the second and third aspects of the invention, in step (i) (or, where relevant, step (ia) and/or step (ib)) of the process the mixture is heated to a temperature of from 40° C. to the boiling point of the mixture. In particular, the mixture may be heated to the boiling point of the mixture. Such temperatures may be from 40 to 70° C. (such as from 50 to 65° C., for example around 65° C.).

In a yet further embodiment of the second and third aspects of the invention, in step (i) (or, where relevant, step (ia) and/or step (ib)) of the process the mixture may be heated at increased (i.e. greater than atmospheric) pressure (for example, at temperatures discussed in respect of the embodiment mentioned directly above or at the boiling point at the mixture at the relevant increased pressure).

In certain embodiments of the second and third aspects of the invention that may be mentioned, the process is conducted in the substantial absence of:
(a) a carboxylic acid (i.e. a molecule (compound) that contains at least one carboxylic acid group (i.e. in which the acidic proton is present)), such as a carboxylic acid corresponding to the carboxylic acid salt of component (c); and/or
(b) a strong base.

As used herein, the term "substantial absence" can be taken as referring to the presence of less than 5% by weight (such as less than 2%, particularly less than 1%, and more particularly less than 0.1% by weight) of the substance referred to.

As used herein, the term "strong base" refers to a substance that is sufficiently basic that it could deprotonate (e.g. achieve more than 50% deprotonation of) a carboxylic acid (such as the corresponding carboxylic acid of a carboxylic acid salt falling within the definition of component (c) above). For example, such bases may have a p$K_b$ (in water at 25° C.) of less than 4 (e.g. less than 3 or, particularly, less than 2). Such bases may include hydroxides, such as sodium hydroxide and potassium hydroxide.

In a certain embodiment of the second and third aspects of the invention that may be mentioned, the process is performed using only one or more pre-formed carboxylic acid salts in respect of component (c) (and therefore does not involve forming component (c) in situ).

In a certain embodiment of the first, second and third aspects of the invention (including all embodiments thereof), the composition may be referred to as being:
(i) a solid; and/or
(ii) a gel.

As used herein, the term "gel" takes its true meaning, and therefore includes references to substantially dilute cross-linked systems that exhibit no flow. Such gels may also be referred to as a "true gel".

As used herein, the term "solid" takes its normal meaning, and therefore includes references to substances demonstrating (significant) structural rigidity and resistance to changes of shape or volume (e.g. substances which exhibit no flow). In particular, the term "solid" may refer to substances characterised by their resistance to penetration. For example, when examined under the procedure set out at Example H below, such "solid" substances may be found to have a yield point of greater than 200 grams (for example, greater than 250 grams) or, in certain cases, greater than 400 grams (for example, greater than 450 grams, such as greater than 800 grams).

In a further embodiment of the first, second and third aspects of the invention (including all embodiments thereof), the composition may be referred to as being amorphous.

As used herein, the term "amorphous" takes its normal meaning, and therefore includes references to a non-crystalline solid.

In a yet further embodiment of the first, second and third aspects of the invention (including all embodiments thereof), the composition may be referred to as being homogeneous.

In view of the above, the skilled person will understand that more than one description of the composition may apply. For example, the composition may be homogenous and a gel (and/or a solid).

In a certain embodiment of the first, second and third aspects of the invention (including all embodiments thereof), the composition may be referred to as being flammable. Such compositions may also be referred to as being combustible. In particular, either term will be understood as including references to a substance that ignites and burns upon application of a source of ignition (e.g. a naked flame) and when in contact with atmospheric oxygen (for example, at atmospheric pressure and at 15° C.).

Particular embodiments of the first, second and third aspects of the invention (i.e. compositions of the first and second aspects of the invention, and processes of the third aspect of the invention) that may be mentioned include those of Examples A to G herein.

Compositions of the invention may be useful as fuels (for example, as solid fuels and/or fuel gels). The skilled person will therefore understand that compositions of the invention may be described as "a solid fuel composition", "a fuel gel composition" and/or "a gel fuel composition".

Thus, in a fourth aspect of the invention there is the use of a composition as defined in respect of first and/or second aspects of the invention (including all embodiments thereof) as a fuel (such as the use as a solid fuel and/or as a fuel gel).

Further, in a fifth aspect of the invention, there is a method of generating heat comprising the step of igniting (or causing to be ignited) a composition as defined in respect of first and/or second aspects of the invention (including all embodiments thereof).

Due to their high alcohol content, compositions of the invention may be useful as sanitizing agents (for example, as hand and/or surface sanitizing agents).

Thus, in a sixth aspect of the invention there is the use of a composition as defined in respect of first and/or second aspects of the invention (including all embodiments thereof) as a sanitizing agent (for example, as a hand and/or surface sanitizing agent).

Further, in a seventh aspect of the invention, there is a method of sanitizing a surface comprising the step of applying to that surface a composition as defined in respect of first and/or second aspects of the invention (including all embodiments thereof).

As used herein, the term sanitizing takes its normal meaning, and therefore includes references to the agent causing a reduction in the amount of bacteria present on the surface to the composition is applied. In this regard, the skilled person will understand that the level of reduction in the amount of bacteria on a surface can be determined by measuring the amount of bacteria on said surface, using techniques known to those skilled in the art, before and after application of the composition as defined in respect of first and/or second aspects of the invention (including all embodiments thereof). The level of reduction in the amount of bacteria may be defined as a 50% reduction in the number of bacterial cells on within a particular area of said surface to which the composition has been applied (such as 80% or more particularly 90% (e.g. 99%)).

In respect of the seventh aspect of the invention, the term "applying" includes references to rubbing the composition on the surface to which it is being applied.

As indicated above, in a particular embodiment of the seventh aspect of the invention, the surface is an area of skin (such as human skin, for example a human hand).

Particular embodiments of the seventh aspect of the aspect of the invention that may be mentioned include those in which the composition further comprises an antibacterial agent (such as Triclosan).

Compositions of the invention may be provided as part of products comprising such compositions contained within a packaging material.

Thus, in an eighth aspect of the invention there is provided a product comprising:
(I) a composition as defined in respect of the first and/or second aspects of the invention (including all embodiments thereof); and
(II) a packaging material,
wherein the composition (I) is at least partially contained within the packing material (II).

In a particular embodiment of the eighth aspect of the invention, the packaging material is made of a combustible material. In particular, the packaging material may be formed from paper (such as wax-coated paper) and/or plastic. For example, the packaging may be designed such that the composition (I) may be ignited via ignition of the packaging material (II).

In a further embodiment of the eight aspect of the invention, the product may consist of multiple (i.e. more than one, such as from 2 to 100) discrete units of the composition (I) (such as multiple sachets or sealed tubs containing the composition (I)).

In particular products that may be provided in accordance with the eighth aspect of the invention, the composition of the invention may be packed in 20 mL to 100 mL (e.g. 35 mL) burnable sachets with a ethanol resistant lining (e.g. to meet air freight hazard regulations). Such sachets (e.g. where 35 mL sachets, having a 30 g approximate weight) may be packed in burnable cartons (possibly waxed) containing 8 or 10 (particularly 8) such sachets. These can be bulk packed in cardboard boxes to a maximum of 10 kg (although the scope could be widened in the bulk pack to a 12 kg absolute maximum).

Compositions of the invention and products comprising such compositions may also form a part of larger products designed for the burning of such compositions.

Thus, in a ninth aspect of the invention there is provided a kit-of-parts comprising:
(A) a composition as defined in respect of the first and/or second aspects of the invention (including all embodiments thereof), or
a product as defined in respect of the eighth aspect of the invention (including all embodiments thereof); and
(B) a cooking apparatus,
wherein component (A) is configured for use with the cooking apparatus (B).

In a particular embodiment of the ninth aspect of the invention, the cooking apparatus (B) is selected from the group consisting of a portable stove (such as a camping stove), an indoor fire, an outdoor food cooking apparatus and a plate warmer.

In a certain embodiment of the eighth and ninth aspects of the invention that may be mentioned, the product is configured for use as a firelighter.

Compositions of the invention may have the advantage that the compositions formed exhibit no flow and, therefore, reduce the risk of leakage from any packaging material (e.g. during storage and/or transport).

Compositions of the invention may also have the advantage the compositions have substantial structural rigidity (i.e. are resistant to crumbing) and that compression and/or sheering of the composition does not cause a substantial degree of the alcohol and/or water component to be expelled from the composition.

Further, compositions of the invention may have the advantage that they may be formed from formed from materials that may have a natural origin, do not produce highly toxic gases (i.e. gases that are poisonous at low concentration) upon combustion, and that such compositions may be obtainable (e.g. formed) via a process that does not require the use of a strong base (such as sodium hydroxide). In view of these advantages, the compositions and process for their production may be described as "green".

Without wishing to be bound by theory, the advantageous properties of the compositions according to the present invention are believed to derive from the ability of the essential cellulose derivative (component (b)) to increase the solubility of and stabilise the essential carboxylic acid salt (component (c)) in the presence of the other components. This results in the cellulose and carboxylic acid components forming a stable matrix within which the alcohol component (component (a)) and, if present, water is provided.

Particular embodiments of the invention (i.e. of the first to ninth aspects of the invention) that may be mentioned include those indicated in the following numbered paragraphs.

Paragraph 1. A composition comprising:
(a) from about 60 to about 98% by weight of one or more alcohols;
(b) from about 0.5 to about 20% by weight of one or more alkyl cellulose derivatives, wherein each alkyl is optionally substituted with one or more OH, O-alkyl, O-hydroxyalkyl and/or O-alkoxyalkyl;
(c) from about 1 to about 25% by weight of one or more carboxylic acid salts; and
(d) from 0 to about 30% by weight of water.

Paragraph 2. A composition as defined in Paragraph 1, wherein component (a):
(a) consists of one or more $C_1$-$C_8$ (e.g. $C_1$-$C_4$) linear or branched (particularly, linear) alkyl moieties substituted with at least one (such as two or, particularly, one) hydroxyl group(s);
(b) consists of one or more liquid alcohols.

Paragraph 3. A composition as defined in Paragraph 1 or Paragraph 2, wherein component (a) consists of one or more (e.g. one or two) alcohols selected from the group consisting of: ethanol, methanol and 2-propanol; and/or the alcohol component of industrial methylated spirits.

Paragraph 4. A composition as defined in any one of Paragraphs 1 to 3, wherein component (a) consists of:
ethanol;
a mixture of ethanol and 2-propanol (e.g. wherein the mixture consists of about 0.5 to 10% (such as about 5%) by weight of 2-propanol and the remainder of the mixture is ethanol); or
a mixture of ethanol and methanol (such as denatured ethanol, and/or wherein the mixture consists of about 0.5 to 20% (such as about 10%) by weight of methanol and the remainder of the mixture is ethanol).

Paragraph 5. A composition as defined in any one of Paragraphs 1 to 4, wherein component (a) is present in an amount that is about 65 to 95% by weight (i.e. the percentage by weight of the combined weight of components (a) to (d) in the composition), such as:
70 to 92% or, particularly, 75 to 90% (e.g. 79 to 89% or 79 to 90%, such as about 90%) by weight; or
70 to 95% or, particularly, 75 to 95% (e.g. 79 to 95%, such as about 89 to 95% (e.g. about 94%) by weight.

Paragraph 6. A composition as defined in any one of Paragraphs 1 to 5, wherein component (b) consists of one or more O-alkyl cellulose derivatives and/or O-hydroxyalkyl cellulose derivates.

Paragraph 7. A composition as defined in any one of Paragraphs 1 to 6, wherein component (b) consists of one or more alkyl cellulose derivates represented by formula I,

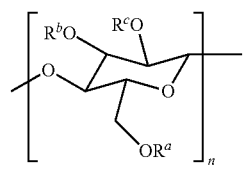

wherein: each of $R^a$ to $R^c$ is independently H or a $C_{1-6}$ (e.g. $C_{1-3}$) alkyl group optionally substituted with one or more (e.g. one) OH group, provided that at least one of $R^a$ to $R^c$ is other than H in at least 20% (e.g. in at least 30, 40, 50 or 60%) of the monomers present; and n is a suitable integer representing the number of glucose monomers present in the cellulose polymer.

Paragraph 8. A composition as defined in any one of Paragraphs 1 to 7, wherein the alkyl cellulose derivative has a DS of from 0.2 to 3 (such as from 1 to 2.8, e.g. from 1.3 to 2.6).

Paragraph 9. A composition as defined in any one of Paragraphs 1 to 8, wherein component (b) consists of one or more (e.g. one or two) alkyl cellulose derivatives selected from the group consisting of hydroxyethyl cellulose, hydroxyethyl methyl cellulose, methyl cellulose, hydroxypropyl cellulose and hydroxypropylmethyl cellulose (for example, wherein component (b) consists of hydroxypropylmethyl cellulose).

Paragraph 10. A composition as defined in any one of Paragraphs 1 to 9, wherein component (b) is present in an amount that is about 0.7 to 10% by weight (i.e. the percentage by weight of the combined weight of components (a) to (d) in the composition), such as 0.8 to 5% or, particularly, 1 to 3% (e.g. 1.1 to 2.5%, such as about 1.2%) by weight.

Paragraph 11. A composition as defined in any one of Paragraphs 1 to 10, wherein component (c) consists of one or more (such as one or two) carboxylic acid salts having a counter ion selected from the group consisting of $Ca^{2+}$, $Li^+$, $K^+$ and $Na^+$ (in particular, $Na^+$).

Paragraph 12. A composition as defined in any one of Paragraphs 1 to 11, wherein component (c) consists of one or more (such as one or two) carboxylic acid salts formed from $C_{10}$-$C_{20}$ (saturated or unsaturated) alkyl carboxylic acids.

Paragraph 13. A composition as defined in any one of Paragraphs 1 to 12, wherein component (c) consists of one or more (such as one or two) carboxylic acid salts formed from $C_{10-20}$ (e.g. $C_{12-20}$, $C_{10-18}$, $C_{14-20}$ or $C_{14-18}$, such as $C_{16-18}$ or $C_{16}$ and/or $C_{18}$) alkyl, $C_{10-20}$ (e.g. $C_{12-20}$, $C_{10-18}$, $C_{14-20}$ or $C_{14-18}$, such as $C_{16-18}$ or $C_{16}$ and/or $C_{18}$) alkenyl or $C_{10-20}$ (e.g. $C_{12-20}$, $C_{10-18}$, $C_{14-20}$ or $C_{14-18}$, such as $C_{16-18}$ or $C_{16}$ and/or $C_{18}$) alkynyl carboxylic acids (in particular, one or more (such as one or two) carboxylic acid salt obtainable from (e.g. formed from) a $C_{10}$-$C_{20}$ (e.g. $C_{12-20}$, $C_{10-18}$, $C_{14-20}$ or $C_{14-18}$, such as $C_{16-18}$ or $C_{16}$ and/or $C_{18}$) alkyl (in particular, a linear alkyl) having one carboxylic acid moiety).

Paragraph 14. A composition as defined in any one of Paragraphs 1 to 13, wherein component (c) is represented by formula II,

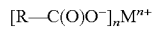

$$[R-C(O)O^-]_n M^{n+} \qquad II$$

wherein: R represents $C_{10-20}$ (e.g. $C_{12-20}$, $C_{10-18}$, $C_{14-20}$ or $C_{14-18}$, such as $C_{16-18}$ or $C_{16}$ and/or $C_{18}$) alkyl, $C_{10-20}$ (e.g. $C_{12-20}$, $C_{10-18}$, $C_{14-20}$ or $C_{14-18}$, such as $C_{16-18}$ or $C_{16}$ and/or $C_{18}$) alkenyl or $C_{10-20}$ (e.g. $C_{12-20}$, $C_{10-18}$, $C_{14-20}$ or $C_{14-18}$, such as $C_{16-18}$ or $C_{16}$ and/or $C_{18}$) alkynyl (in particular, $C_{10-20}$ alkyl); M represents a metal selected from the group consisting of Ca, Li, K and Na (in particular, Na); where M represents Li, K and Na, n represents 1; and where M represents Ca, n represents 2.

Paragraph 15. A composition as defined in any one of Paragraphs 1 to 14, wherein component (c) consists of one or two carboxylic acid salts selected from the group consisting of sodium palmitate and sodium stearate (for example, wherein component (c) consists of sodium stearate).

Paragraph 16. A composition as defined in any one of Paragraphs 1 to 15, wherein component (c) consists of:
(a) a mixture of sodium palmitate and sodium stearate (such as a roughly equal mixture); or
(b) sodium stearate.

Paragraph 17. A composition as defined in any one of Paragraphs 1 to 16, wherein component (c) is present in an amount that is about 1 to 15% by weight (i.e. the percentage by weight of the combined weight of components (a) to (d) in the composition), such as 2 to 10% or, particularly, 3 to 6% (e.g. 3.7 to 5.4%) or 3 to 5% (e.g. about 4 to 5%, such as 4.4% or 4.6%) by weight.

Paragraph 18. A composition as defined in any one of Paragraphs 1 to 3, wherein:
component (d) is 0 to about 25% by weight (i.e. the percentage by weight of the combined weight of components (a) to (d) in the composition), such as 0 to 20.0% or, particularly, 0 to 15.0% (e.g. 0 to 14.8%, such as about 4.5%) by weight;
component (d) is present in an amount that is about 1 to 25% by weight, such as 2 to 20% or, particularly, 5 to 15% (e.g. 5.6 to 14.8%) or 4 to 15% (for example, about 3 to 6%, such as about 4 to 5%, e.g. about 4.5%) by weight; or
component (d) is present in an amount that is less than about 10% (e.g. less than about 5%, particularly less than about 1%) by weight.

Paragraph 19. A composition as defined in Paragraph 1, wherein the composition comprises:
(a) from about 60 to about 98% (such as about 65 to 95%, 70 to 92% or, particularly, 75 to 90%) by weight of
  (i) one or more alcohols selected from the group consisting of ethanol, methanol and 2-propanol, or
  (ii) the alcohol component of industrial methylated spirits;
(b) from about 0.7 to 10% (such as 0.8 to 5% or, particularly, 1 to 3%) by weight of one or more (e.g. one or two) cellulose derivatives selected from the group consisting of hydroxyethyl cellulose, hydroxyethyl methyl cellulose, methyl cellulose, hydroxypropyl cellulose and hydroxypropylmethyl cellulose;
(c) from about 1.5 to 15% (such as 2 to 10% or, particularly, 3 to 6%) by weight of one or more carboxylic acid salts selected from the group consisting of sodium palmitate and sodium stearate (such as a roughly equal mixture of sodium palmitate and sodium stearate); and
(d) from 0 to about 25% (such as 0 to 20% or, particularly, 0 to 15%, e.g. 0 to about 5%) by weight, or alternatively about 1 to 25% (such as 2 to 20%, 5 to 15% or, particularly, 4 to 15%) by weight, of water.

Paragraph 20. A composition obtainable via a process involving forming a homogenous mixture of components (a) to (d) as defined in any one or more of Paragraphs 1 to 19.

Paragraph 21. A composition as defined in any one of Paragraphs 1 to 19, wherein the composition further comprises one or more additives selected from the group consisting of colorants, stabilizing agents, taste modifiers (such as bitter tasting substances, e.g. denatonium benzoate (Bitrex®)), antibacterial agents and, optionally, denaturing agents, antifungal agents, powdered metal(s) and activated charcoal.

Paragraph 22. A composition as defined in any one of Paragraphs 1 to 21, wherein the composition consists of components (a) to (d) (and, optionally, a colorant, stabilizing agent, taste modifier, antibacterial agent, denaturing agent, antifungal agent, powdered metal(s) and/or activated charcoal, such as a colorant, stabilizing agent, taste modifier and/or antibacterial agent).

Paragraph 23. A composition as defined in any one of Paragraphs 1 to 22, wherein the composition is described as being one or more of the following:
(i) a solid;
(ii) a gel;
(iii) amorphous;
(iv) homogeneous;
(v) flammable;
(vi) combustible.

Paragraph 24. A process for preparing a composition as defined in any one of Paragraphs 1 to 23, wherein the process comprises forming a homogenous mixture of components (a) to (d) as defined in any one or more of Paragraphs 1 to 19, and wherein the process for forming the composition comprises the steps of:
(i) heating a mixture comprising at least some of (e.g. all of) each of components (a) to (c) and, where present, component (d), until the mixture becomes homogenous; and
(ii) cooling the mixture so obtained.

Paragraph 25. A process as defined in Paragraph 24, wherein step (i) consists of the steps of:
(ia) heating a mixture of at least some of (e.g. all of) each of components (a) and (b) and, where present, component (d), until component (b) is dissolved in component (a); and then
(ib) adding at least some of (e.g. all of) component (c) and heating until the mixture becomes homogenous.

Paragraph 26. A process as defined in Paragraph 24 or Paragraph 25, wherein in step (i) (or, where relevant, step (ia) and/or step (ib)) of the process the mixture is heated to a temperature of from 40° C. to the boiling point of the mixture (for example, to the boiling point of the mixture), such as from 40 to 70° C. (e.g. from 50 to 65° C., in particular around 65° C.)).

Paragraph 27. A process as defined in any one of Paragraphs 24 to 26, wherein the process is conducted in the substantial absence of:
(a) a carboxylic acid (i.e. a molecule (compound) that contains at least one carboxylic acid group (i.e. in which the acidic proton is present)), such as a carboxylic acid corresponding to the carboxylic acid salt of component (c); and/or
(b) a strong base.

Paragraph 28. The use of a composition as defined in any one of Paragraphs 1 to 23 as a fuel (such as the use as a solid fuel and/or as a fuel gel).

Paragraph 29. A method of generating heat comprising the step of igniting (or causing to be ignited) a composition as defined in any one of Paragraphs 1 to 23.

Paragraph 30. The use of a composition as defined in any one of Paragraphs 1 to 23 as a sanitizing agent (for example, as a hand and/or surface sanitizing agent).

Paragraph 31. A method of sanitizing a surface comprising the step of applying to that surface a composition as defined in any one of Paragraphs 1 to 23.

Paragraph 32. A product comprising:
(I) a composition as defined in any one of Paragraphs 1 to 23; and
(II) a packaging material,
wherein the composition (I) is at least partially contained within the packing material (II).

Paragraph 33. A product as defined in Paragraph 32, wherein the packaging material is made of a combustible material (e.g. paper (such as wax-coated paper) and/or plastic).

Paragraph 34. A product as defined in Paragraph 32 or Paragraph 33, wherein the product consists of multiple (i.e. more than one, such as from 2 to 100) discrete units of the composition (I) (such as multiple sachets or sealed tubs containing the composition (I)).

Paragraph 35. A kit-of-parts comprising:
(A) a composition as defined in any one of Paragraphs 1 to 23, or
a product as defined in any one of Paragraphs 32 to 34; and
(B) a cooking apparatus,
wherein component (A) is configured for use with the cooking apparatus (B).

EXAMPLES

Figure 1:
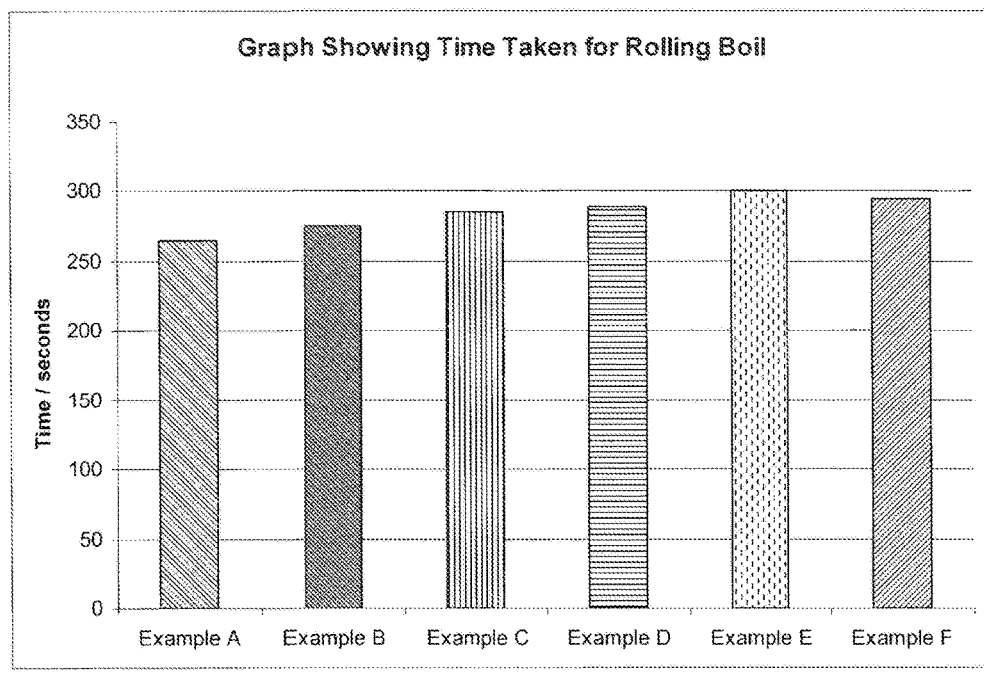
FIG. 1 shows the results of the experiment described as Example G.

In each example referred to below, the sodium palmitate/stearate mixture was obtained from Acros Organics (identified in the relevant Materials Safety Data Sheet (MSDS) as "Stearic acid, sodium salt, mixture of stearic and palmitic fatty chain", Cat No. 269880000; 269880010, Synonyms: Octadecanoic acid, sodium salt; Sodium stearate).

Example A

Hydroxypropyl cellulose (4.00 g, 150-400 mPa·s, obtained from TCI UK) was slowly added to a stirring mixture of ethanol (180 mL) and distilled water (20 mL) at room temperature. When the mixture was homogeneous it was heated (65° C.) and sodium palmitate/stearate mixture (14.00 g, obtained from Acros) was slowly added and stirring continued until the mixture was homogeneous. Further aliquots of ethanol (180 mL) and 2-propanol (20 mL) were added with continuous heating and stirring and then the mixture was cast into small blocks and allowed to cool, upon which the mixture solidified into an opaque/colourless solid.

Example B (Hydroxypropyl)methylcellulose (2.00 g, 40-60 mPa·s, obtained from Alfa Aesar) was slowly added to a stirring mixture of Ethanol/2-propanol (50 mL of a 95:5 v/v mixture), distilled water (10 mL) and then heated (65° C.) until homogeneous. Sodium palmitate/stearate mixture (7.50 g, obtained from Acros) was slowly added and stirring continued until the mixture was homogeneous. A further aliquot of Ethanol/2-propanol (150 mL of a 95:5 v/v mixture) was added with continuous heating and stirring. The mixture was cast into small blocks and allowed to cool, upon which the mixture solidified into an opaque/colourless solid.

Example C

Methylcellulose (2.50 g, 4000 mPa·s, obtained from Alfa Aesar) was slowly added to a stirring mixture of IMS (50 mL), distilled water (10 mL) and then heated (65° C.) until homogeneous. A further aliquot of IMS (50 mL) was added along with sodium palmitate/stearate mixture (7.50 g, obtained from Acros) and the stirring was continued until the mixture was homogeneous. A final aliquot of IMS (100 mL) was added with continuous heating and stirring. The mixture was cast into small blocks and allowed to cool, upon which the mixture solidified into an opaque/colourless solid.

Example D

Methylcellulose (5.00 g, 1600 mPa·s, obtained from Alfa Aesar) was slowly added to a stirring mixture of IMS (200 mL), distilled water (30 mL) and then heated (65° C.) until homogeneous. Sodium palmitate/stearate mixture (7.50 g, obtained from Acros) was slowly added and stirring continued until the mixture was homogeneous. The mixture was cast into small blocks and allowed to cool, upon which the mixture solidified into an opaque/colourless solid.

Example E

Methylcellulose (2.50 g, 4000 mPa·s, obtained from Alfa Aesar) was slowly added to a stirring mixture of ethanol (45 mL), distilled water (20 mL) and stirred at room temperature for 24 h, until homogeneous. A further aliquot of ethanol (45 mL) was added and the mixture was heated to 65° C. and stirred vigorously. Sodium palmitate/stearate mixture (7.50 g, obtained from Acros) and was slowly added and stirring continued for 1 h. Ethanol (90 mL) and 2-propanol (20 mL) was added with continuous heating and stirring. The mixture was cast into small blocks and allowed to cool, upon which the mixture solidified into an opaque/colourless solid.

Example F

Ethylcellulose (2.00 g, Sigma Aldrich) was slowly added to a stirring mixture of Ethanol/2-propanol (50 mL of a 95:5 v/v mixture), distilled water (10 mL) and then heated (65° C.) until homogeneous. Sodium palmitate/stearate mixture (7.50 g, obtained from Acros) was slowly added and stirring continued until the mixture was homogeneous. A further aliquot of ethanol/2-propanol (150 mL of a 95:5 v/v mixture) was added with continuous heating and stirring. The mixture was cast into small blocks and allowed to cool, upon which the mixture solidified into an opaque/colourless solid.

Example G

Burn Test

Water (500 mL) at 15° C. was placed into a standard issue stainless steel mug (Model CN540 with lid attached). 60 grams of each compositions of Examples A to E were placed into a variant of BCB International's Crusader Cooker (Model RP006, modified with 2×30 holes of 5 mm diameter) and this was ignited and the mug was placed on top immediately. The end point of the test was determined by a constant roiling boil of the water. All tests were carried out in identical atmospheric conditions in the same apparatus and performed by one individual for reproducibility of the data. The results are shown in Table 1 (below) and in FIG. 1.

TABLE 1

| Example | Time to Rolling Boil (Seconds) |
|---------|-------------------------------|
| A | 265 |
| B | 275 |
| C | 286 |
| D | 289 |
| E | 301 |
| F | 295 |

Example H

Penetration Test

Figure 2A:
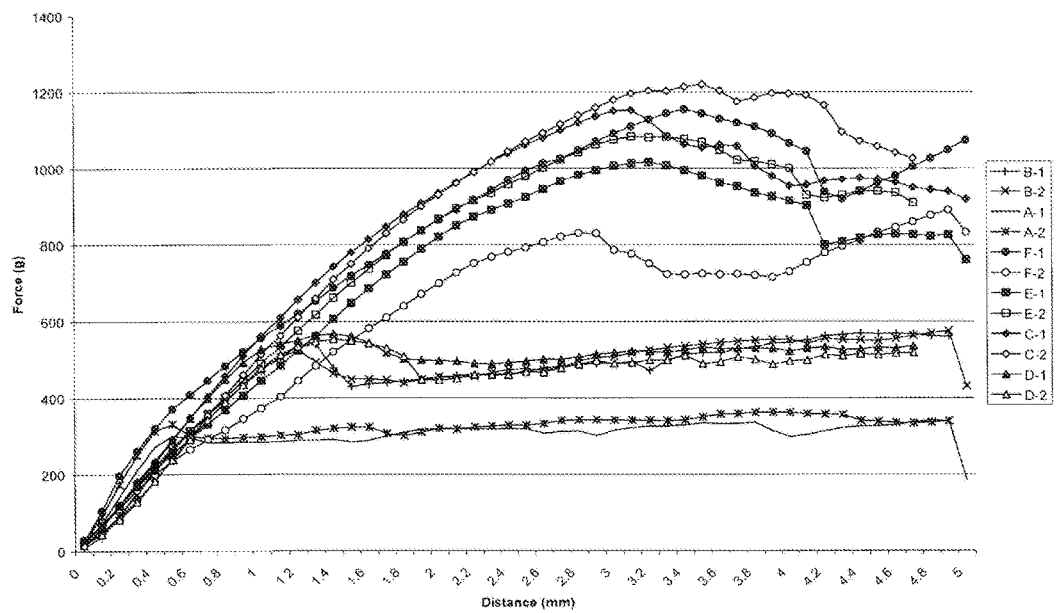
FIG. 2 shows the results of the experiment described as Example H.
Figure 2B:
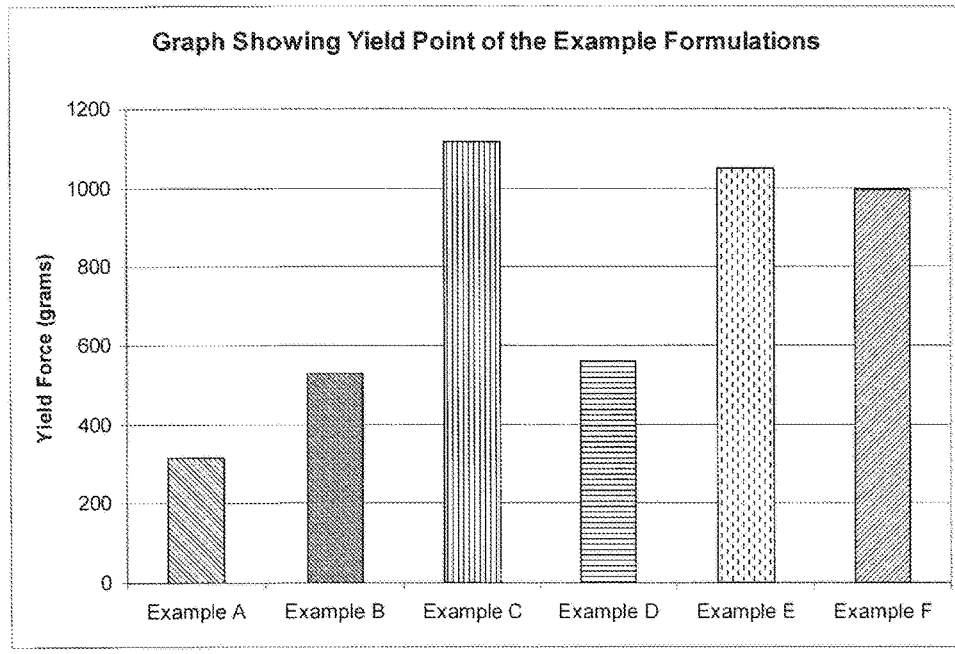

Tests were conducted in respect of each of Examples A to E. In each case, a probe (6 mm diameter) was lowered onto the sample at 0.05 mm/second. The distances moved by the probe into the sample (the degree of penetration) was measured in comparison to the degree of force required to sustain the speed of movement. The results are shown in FIG. 2A. An inflexion (e.g. a sudden decrease) in the force required to move further indicates the yield point of the sample. The yield point of each sample is shown in FIG. 2B.

Example I

Ethanol (182 mL), water (8 mL), and isopropanol (10 mL) were heated to 70° C. To this was added hydroxypropyl methylcellulose (2.00 g; 40-60 mPa·s, obtained from Alfa Aesar), and stirred for 30 minutes. Sodium palmitate/stearate mixture (7.50 g; obtained from Acros) was added and the solution stirred until all solids had dissolved (~30 minutes). To this was added activated charcoal powder (2.00 g), and the mixture stirred for 10 minutes. The liquid was cast into small blocks and upon cooling solidified into a black solid.

Similar compositions have been prepared using up to 4.00 g activated charcoal powder.

Example J

Compositions were prepared in accordance with the methods used in Example B using the following components:
ethanol TSDA 7 (1000 mL) (consisting of IPA (50 mL), water (38.4 mL) and ethanol (911.6 mL));
hydroxypropyl methylcellulose (10 g; 40-60 mPa·s, obtained from Alfa Aesar); and sodium palmitate/stearate mixture (37.5 g; obtained from Acros).

Similar compositions may be prepared wherein 0.08% of the ethanol TSDA 7 is replaced with a 0.256% solution of denatonium benzoate (Bitrex®).

Example K

Compositions were prepared in accordance with the methods used in Example B using the following components:
completely denatured alcohol (CDA) (1000 mL) (consisting of IPA (~28 mL), butanone (~28 mL) and ethanol (~942 mL));
hydroxypropyl methylcellulose (10 g; 40-60 mPa·s, obtained from Alfa Aesar); and
sodium palmitate/stearate mixture (37.5 g; obtained from Acros).

Similar compositions may be prepared wherein small amounts of denatonium benzoate (Bitrex®) and/or methyl violet are present in the CDA.

What is claimed is:

1. A composition comprising:
   (a) from about 60 to about 98% by weight of one or more alcohols consisting of one or more $C_1$-$C_4$ linear or branched alkyl moieties substituted with one or two hydroxyl group(s);
   (b) from about 0.5 to about 20% by weight of one or more alkyl cellulose derivatives, wherein each alkyl is optionally substituted with one or more OH, O-alkyl, O-hydroxyalkyl and/or O-alkoxyalkyl;
   (c) from about 1 to about 25% by weight of one or more carboxylic acid salts formed from $C_{10-20}$ alkyl, $C_{10-20}$ alkenyl or $C_{10-20}$ alkynyl carboxylic acids; and
   (d) from 0 to about 30% by weight of water.

2. A composition as claimed in claim 1, wherein component (a) consists of one or more alcohols selected from the group consisting of: ethanol, methanol and 2-propanol; and/or the alcohol component of industrial methylated spirits.

3. A composition as claimed in claim 1, wherein component (b) consists of one or more O-alkyl cellulose derivatives and/or O-hydroxyalkyl cellulose derivatives.

4. A composition as claimed in claim 1, wherein component (b) consists of one or more cellulose derivatives selected from the group consisting of hydroxyethyl cellulose, hydroxyethyl methyl cellulose, methyl cellulose, hydroxypropyl cellulose and hydroxypropylmethyl cellulose.

5. A composition as claimed in claim 1, wherein component (c) consists of one or more carboxylic acid salts having a counter ion selected from the group consisting of $Ca^{2+}$, $Li^+$, $K^+$ and $Na^+$.

6. A composition as claimed in claim 1, wherein component (c) consists of one or two carboxylic acid salts selected from the group consisting of sodium palmitate and sodium stearate.

7. A process for preparing a composition as defined claim 1, wherein the process comprises forming a homogenous mixture of:
   (a) from about 60 to about 98% by weight of one or more organic alcohols consisting of one or more $C_1$-$C_4$ linear or branched alkyl moieties substituted with one or two hydroxyl group(s);
   (b) from about 0.5 to about 20% by weight of one or more alkyl cellulose derivatives, wherein each alkyl is optionally substituted with one or more OH, O-alkyl, O-hydroxyalkyl and/or O-alkoxyalkyl;
   (c) from about 1 to about 25% by weight of one or more carboxylic acid salts formed from $C_{10-20}$ alkyl, $C_{10-20}$ alkenyl or $C_{10-20}$ alkynyl carboxylic acids; and
   (d) from 0 to about 30% by weight of water.

8. A method of generating heat comprising the step of igniting (or causing to be ignited) a composition as defined in claim 1.

9. A method of sanitizing a surface comprising the step of applying to that surface a composition as defined in claim 1.

10. A product comprising:
    (I) a composition as defined in claim 1; and
    (II) a packaging material, wherein the composition (I) is at least partially contained within the packing material (II).

11. A kit-of-parts comprising:
    (A) a composition as defined in claim 1, or
       a product comprising the composition as defined in claim 1 and a packaging material, wherein the composition is at least partially contained within the packing material; and
    (B) a cooking apparatus,
wherein component (A) is configured for use with the cooking apparatus (B).

* * * * *